United States Patent [19]

Barr

[11] Patent Number: 5,084,912
[45] Date of Patent: Jan. 28, 1992

[54] METHOD AND APPARATUS FOR GENERATING A NON-CARDIAC ANGIOGRAPH ON A SYSTEM CAPABLE OF GENERATING A CARDIAC ANGIOGRAPH

[75] Inventor: David A. Barr, San Jose, Calif.

[73] Assignee: ADAC Laboratories, Milpitas, Calif.

[21] Appl. No.: 598,386

[22] Filed: Oct. 15, 1990

[51] Int. Cl.$^5$ .............................................. H05G 1/64
[52] U.S. Cl. .................................. 378/99; 378/62; 358/111
[58] Field of Search ......................... 378/62, 98, 99; 358/111

[56] References Cited

U.S. PATENT DOCUMENTS 4,382,184  5/1983  Wernikoff ............................ 378/62
4,444,196  4/1984  Stein ................................... 358/111

OTHER PUBLICATIONS

Seibert, J. Anthony, et al., "Interlaced Versus Progressive Readout of Television Camera for Digital Radiographic Acquisitions", Medical Physics, vol. 11, No. 5, Sep./Oct. 1984.

GE Medical Systems, "ADVANTX: Your Access to the Future of Cardiovascular Imaging", 1987.

GE Product Data, "S5802/3 Advantx Angiovascular System", 11-187, pp. 1-8.

Primary Examiner—Janice A. Howell
Assistant Examiner—David P. Porta
Attorney, Agent, or Firm—Townsend and Townsend

[57] ABSTRACT

A cardiac angiography system is configured to generate a non-cardiac angiograph by generating a blanking signal for a TV camera according to a desired non-cardiac image rate and image accumulation interval, while triggering the X-ray source to generate X-ray pulses typical for a cardiac application. The X-ray pulses are triggered by a shutter signal which has a pulse repetition rate greater than that typically used for a non-cardiac application so as to cause a plurality of X-ray pulses during the accumulation interval of the TV camera. The resulting plurality of X-ray pulse images are accumulated at the TV camera to form a single image frame for the non-cardiac exam. After a specified accumulation time, the TV camera closes the frame, sending the resulting video signal to a computer system for conversion, processing and storage. Resulting image data is used to form a display on a CRT and/or a printout as a hard-copy photograph.

21 Claims, 4 Drawing Sheets

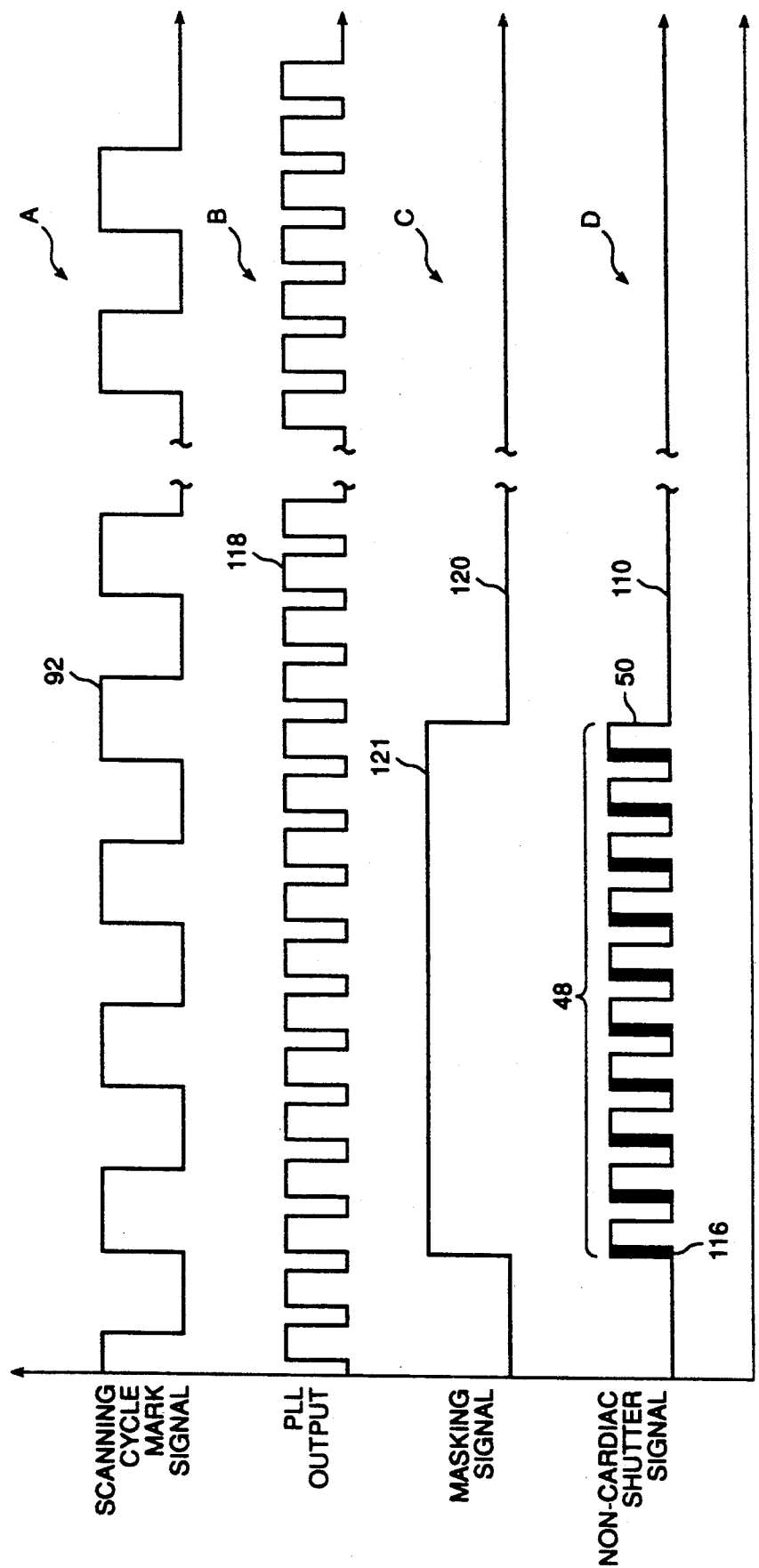

METHOD AND APPARATUS FOR GENERATING A NON-CARDIAC ANGIOGRAPH ON A SYSTEM CAPABLE OF GENERATING A CARDIAC ANGIOGRAPH

BACKGROUND OF THE INVENTION

This invention relates to the generation of radiographs, including cardiac and non-cardiac angiographs. More particularly, this invention relates to a method and apparatus for generating a non-cardiac angiograph on a cardiac angiography system.

A radiograph is an image produced by the emissions, typically X-rays, from a radioactive substance. An angiograph is a radiograph generated by capturing an X-ray image after injecting a radiopaque substance. Cardiac angiography refers to the imaging of the heart, whereas non-cardiac angiography refers to the imaging of other organs and arteries. Cardiac and non-cardiac X-ray images are used for viewing the flow of blood in the heart or other organs and body parts. Because the heart moves rapidly during an examination, many frames of short duration are captured so as to view the dynamic motion of the heart in a group of clear focused images. Because other organs move relatively slow or not at all compared to the heart, fewer frames of longer duration may be captured, while still obtaining clear focused images.

For a conventional cardiac exam implemented with a cardiac angiography system, X-rays are emitted toward a subject. Some of the X-rays are absorbed or scattered, while other X-rays pass through the subject toward an image intensifier. The passed X-rays are converted by the image intensifier to an optical image which, through the use of mirrors and/or beam splitters, is focused at either or both of a film camera (i.e., 35 mm) and a TV camera. The film camera is used for capturing multiple still shots for exposure as individual photographs. The TV camera is used for capturing multiple shots which are converted into digital video image samples, then processed and combined to form a dynamic video image sequence.

For a conventional non-cardiac exam implemented with a non-cardiac angiography system, the functional operation is similar to that as described for the cardiac angiography system. A film camera may be used to capture one or more still photographs, while a TV camera may be used to capture and format a dynamic video image sequence.

For a typical cardiac exam, approximately ten sequences of images may be obtained so as to view the heart at different projections. A single sequence lasts approximately 8 seconds and is formed by a plurality of frames captured generally at a rate of 30 or 60 frames per second (fps), and sometimes at rates as high as 90 fps or 150 fps. Each frame within a sequence is formed by transmitting an X-ray pulse of approximately 2 to 10 milliseconds and capturing the resulting radiograph on the 35 mm film and/or TV camera. For each X-ray pulse of 2 to 10 milliseconds, an X-ray exposure of approximately 20 to 100 micro-Roentgens is achieved as measured at an image intensifier input surface.

For a typical non-cardiac exam, the number and length of sequences may vary. In addition, the number of frames that may form a sequence may vary. Compared to the sequence for a cardiac exam, the sequence for a non-cardiac exam is formed by a plurality of frames captured at a slower rate, such as 1–8 frames per second (fps). In addition, the typical non-cardiac application requires a larger exposure level (i.e., approximately 1000 micro-Roentgens as measured at the surface of the image intensifier). Such exposure level may be achieved with an X-ray pulse of longer duration (i.e., 50 to 100 milliseconds).

The cardiac exam requires shorter pulses and more frames so as to capture the faster motion of the heart in a focused non-blurred image sequence as previously discussed. Such short pulses typically limit the exposure level that can be used for a cardiac exam. For the non-cardiac exam fewer frames and approximately the same number of sequences are needed. Thus a larger exposure level may be used to enhance the quality of the formed image and thereby enable smaller and/or low contrast objects to b discerned.

The differing requirements (e.g., exposure level, exposure duration, frames per second) for acquisition of cardiac and non-cardiac exams result in differences in the systems upon which these exams are performed. A conventional system which supports both types of exams is costlier than a system which only supports one type of exam. Accordingly, a more efficient solution is needed for achieving non-cardiac exams on a system which normally is used for acquiring only cardiac exams.

SUMMARY OF THE INVENTION

According to the invention, a conventional cardiac angiography system is modified to enable both cardiac and non-cardiac angiography.

According to one aspect of the invention, exposure circuitry conventional to a cardiac system is controlled for generating X-rays pulses, while a TV camera is controlled for accumulating a radiograph from a plurality of X-ray pulses.

According to another aspect of the invention, the plurality of X-ray pulse images are accumulated at the TV camera to form a single image frame for the non-cardiac exam. This varies from the conventional method of forming a frame with the image of a single X-ray exposure. After a specified accumulation time, the TV camera closes the frame, sending the resulting video signal to a computer system for conversion, processing and storage. Resulting image data is used to form a display on a CRT and/or a printout as a hard-copy photograph.

According to another aspect of the invention, the image rate (e.g., number of video images/image frames generated per second) may be altered during the course of a non-cardiac exam. The image rate is selected by an operator as an input to the system. During the course of an exam, the operator may vary the image rate. For example the operator may choose to increase the image rate to a higher rate as an injected dye enters an arterial system of particular interest.

BRIEF DESCRIPTION OF THE DRAWINGS

FIG. 5 is a timing diagram of signals which form a shutter signal for a non-cardiac exam according to the system of FIG. 1.

DESCRIPTION OF THE PREFERRED EMBODIMENT

Overview

Figure 1:
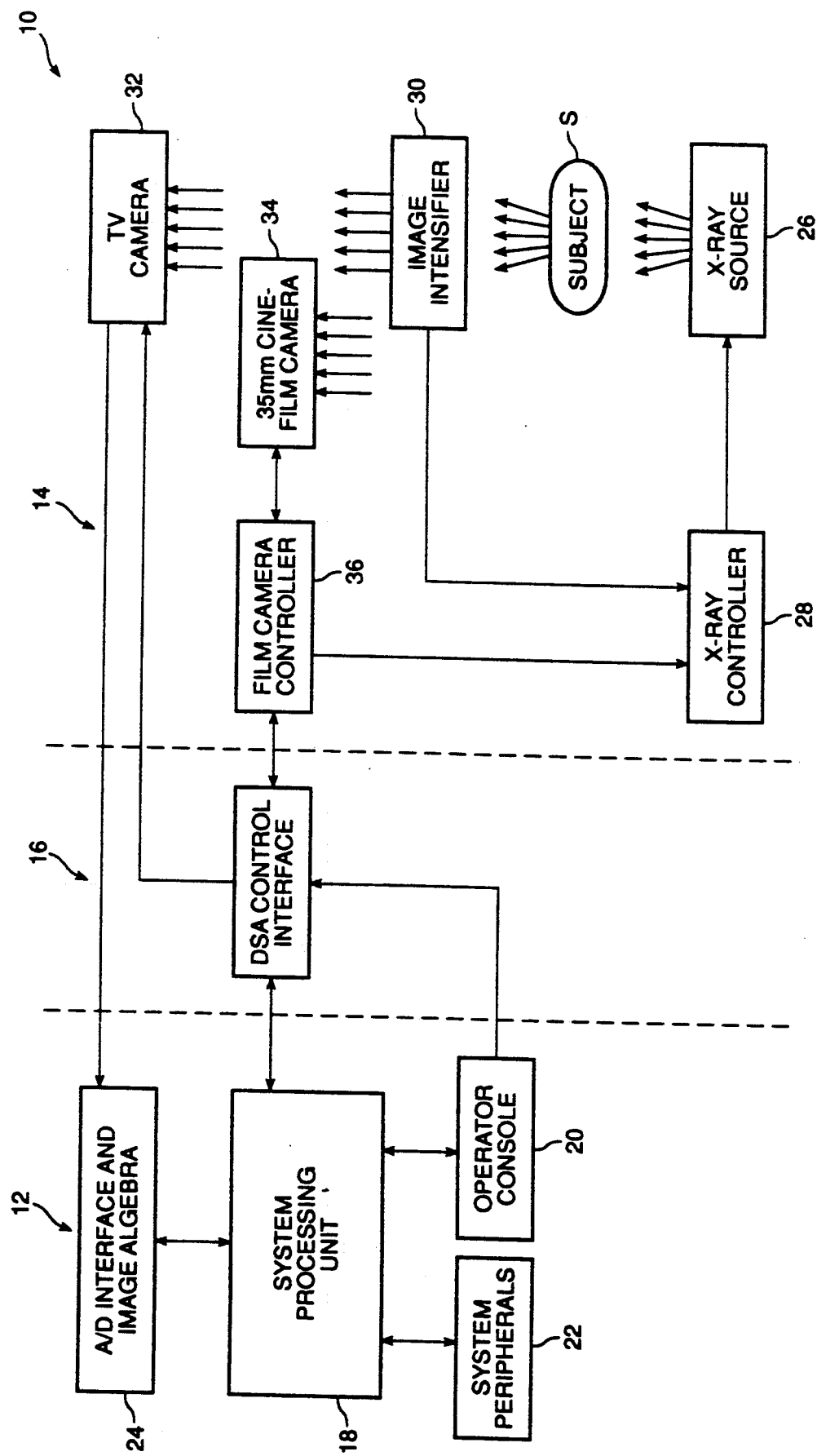
FIG. 1 is a block diagram of a cardiac angiography system as modified according to an embodiment of this invention.

FIG. 1 shows a cardiac angiography system 10 as modified to perform both cardiac and non-cardiac exams. The system 10 includes a computer system 12, an X-ray imaging system 14 and an interface 16.

The computer system 12 includes a system processing unit 18, an operator console 20, system peripherals 22 and an A/D interface and image algebra circuit 24. According to one embodiment, the system processing unit 18 includes a DEC LSI 11/73 central processing unit with one mega-byte of CPU memory, a 22-bit Q bus and a 64-bit video bus. The operator console 20 includes a plasma touchscreen, an alphanumeric keyboard, a remote infrared control keypad and a CRT display. The system peripherals 22 may include a printer for printing still photographs of a video image stored in memory. The A/D interface and image algebra circuitry 24 include A/D circuits for converting analog video signals received from the TV camera 32 into digital signals. The digital signals are processed by a 32-bit floating point processor interfaced to the video bus. The resulting video image data is stored in video memory.

The X-ray imaging system 14 includes X-ray source 26, X-ray controller 28, image intensifier 30, TV camera 32, thirty-five mm cine-film camera 34 and film camera controller 36. For one embodiment a General Electric Advantx L/U-AC system (and/or L/U-C system) forms the imaging system 14 components 26, 28, 30, 34 and 36, while an ADAC DTV-4114 TV camera forms the TV camera 32.

The interface 16 couples signals generated by the computer system 12 to the X-ray imaging system 14. The interface 16 includes added circuitry which generates signals input to the TV camera 32 and to the film camera controller 36 for enabling the system 10 to perform non-cardiac angiography. A conventional camera controller (i.e., of the GE Advantx system) is modified slightly to form the camera controller 36. Such modifications enable the interface 16 to disable the film camera 34 motor and substitute signals for expected film camera 34 status signals. The modifications are simple, including the insertion of a number of jumpers which channel the motor enable signal and the camera 34 status signals through the interface 16.

The television camera 32 is an automated two-piece video camera capable of high resolution imaging (e.g., 512/1024 pixel resolution) over a wide dynamic range (e.g., approximately 1000:1). The camera operates at selectable scanning speeds. The DTV-4114 TV camera allows any of a slow scan speed (e.g., 7.5 fps), standard scan speed (e.g., 30 fps) and fast scan speed (e.g., 60 fps). Camera 32 inputs include a scan speed select signal and a blanking signal from the system processor 18 as derived from operator inputs. The TV camera 32 accumulates at a target surface an image of an optical image produced by image intensifier 30 in response to X-rays. The DTV-4114 TV camera includes a vidicon-type image tube scanned by an electron beam to read the image accumulated at the target layer of the vidicon tube. According to another embodiment, a solid-state TV camera is used which includes a solid-state image sensor (e.g., image array of cells) for accumulating photocharge at each respective cell.

The purpose of the angiography system 10 is to generate video images and film images from X-ray exposures of a subject. The X-ray source 26 emits X-rays which pass through a subject S to an image intensifier 30. The intensifier 30 converts the X-rays which pass through the subject to an optical image (e.g., shadow) to impinge upon either or both of a film camera 34 and a TV camera 32. The film camera 34 captures one or more still photographs or film frames, while the TV camera 32 captures video frames. The film camera 34 produces fixed hard-copy photographs or film, while the TV camera produces electronic analog signals input to the computer system 12 for conversion, processing, storage and display. The processing of digital image data by the system processor 18 to form an angiograph is described in the commonly-assigned U.S. Pat. No. 4,636,850 to Stewart for "Apparatus and Method for Enhancement of Video Images," included herein in its entirety by reference.

The X-ray source 26 has three variable parameters for controlling the X-ray exposures: X-ray pulse width, X-ray tube current and X-ray tube voltage potential. The pulse width determines the duration of the X-ray exposure, while the current and voltage potential determine the intensity of the X-ray exposure. According to one embodiment, the computer 12, based upon an operator input, defines one parameter (e.g., pulse width), while automatic control circuitry controls the other parameters (e.g., X-ray tube current and X-ray tube potential). The automatic control circuitry determines such parameters as part of an operation for regulating the optical exposure of film. The automatic exposure circuitry monitors the brightness of the output image at the image intensifier 30 and controls the X-ray parameters and exposure based upon such monitoring.

For a conventional cardiac system, the pulse width is selectable within a range of 2 to 10 milliseconds. With regard to the current and voltage potential selection, the image intensifier 30 feeds back a signal to the X-ray controller 28 based upon the output brightness of the image intensifier 30. The controller 28 in response modifies the current and/or potential so as to achieve a satisfactory image within operation and safety limits. According to another embodiment, the controller 28 also modifies the X-ray pulse width in response to the output brightness of the intensifier 30.

Figure 2:
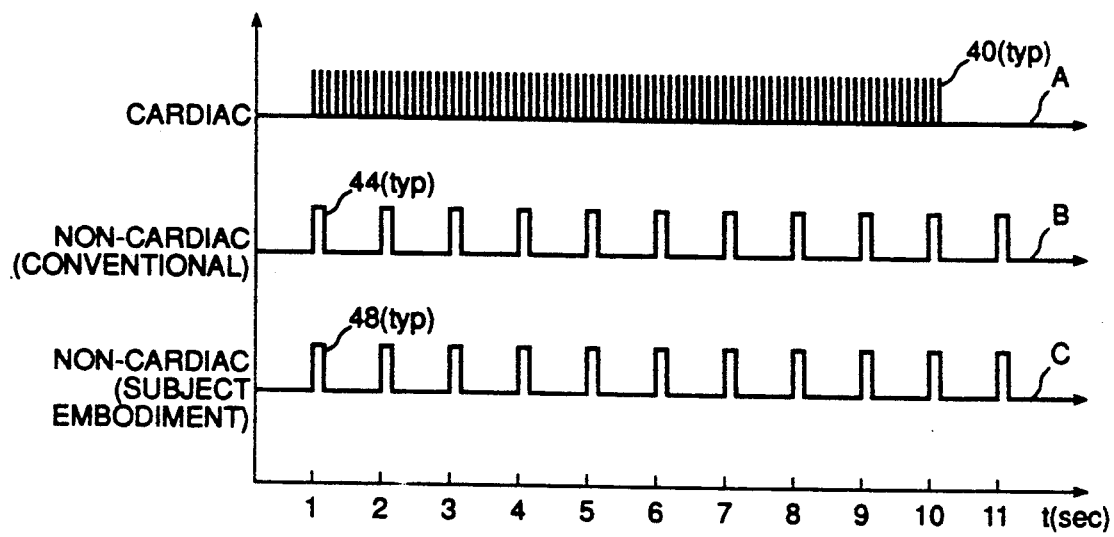
FIG. 2 is a chart depicting a frame sequence for a conventional cardiac exam and a conventional non-cardiac exam and for a non-cardiac exam as implemented by the system of FIG. 1.
Figure 3:
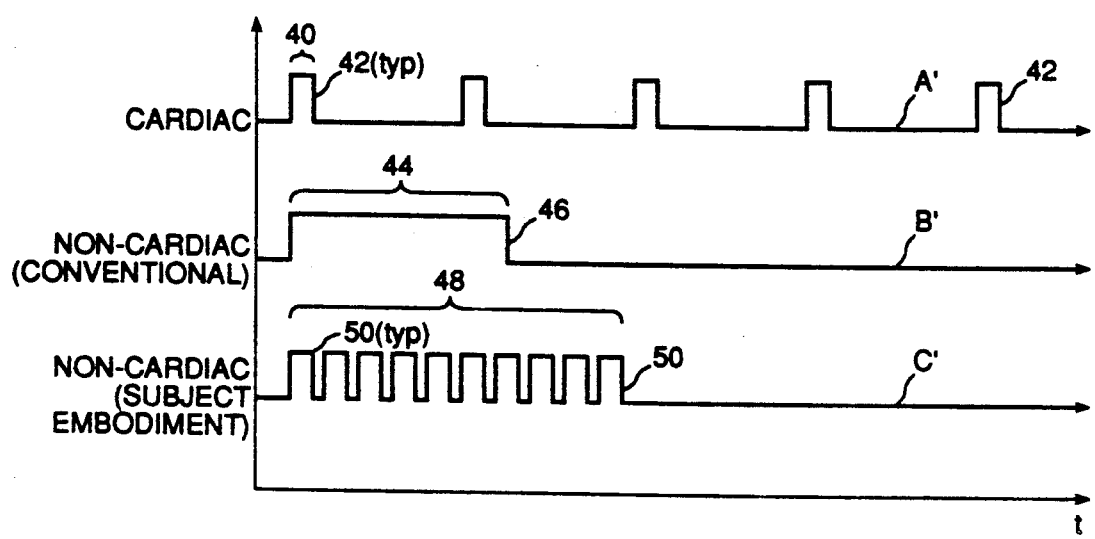
FIG. 3 is a detailed look at the frames for the respective frame sequences of FIG. 2.

FIG. 2 shows a sequence of video frames generated according to conventional cardiac and non-cardiac systems, along with a sequence of frames generated according to an embodiment of this invention. As described in the background of the invention, a cardiac exam includes multiple sequences of approximately eight seconds per sequence. Curve A of FIG. 2 shows one sequence of a conventional cardiac exam. The sequence is formed by a plurality of frames 40 at a rate of 30 frames per second (fps). Conventional frame rates for a cardiac exam range between 30 and 150 fps. Curve A' of FIG. 3 shows a detailed view of each frame 40. As shown, each frame 40 is formed from a single pulse 42 of approximately 5 milliseconds duration. Conventional cardiac systems allow a pulse width range of 2 to 10 milliseconds.

Curve B of FIG. 2 shows a sequence for a conventional non-cardiac exam. The sequence is formed by a plurality of frames 44 at a rate of 1 fps. Conventional frame rates for a non-cardiac exam range between 1 and 8 fps. Curve B' of FIG. 3 shows a detailed view of a frame 44. As shown, each frame 44 is formed from a single pulse 46 of approximately 50 milliseconds duration. Conventionally, such pulse 46 ranges between approximately 30 and 100 milliseconds.

Curve C of FIG. 2 shows a sequence for a non-cardiac exam generated according to an embodiment of this invention. The sequence is formed by a plurality of frames 48 at a rate of 1 fps. Such frame rate may vary between approximately 1 fps and 8 fps. Curve C' of FIG. 3 shows a detailed view of frame 48. As shown, each frame 48 is formed by a plurality of pulses 50 of approximately 10 milliseconds duration each. The pulses 50 may vary in duration according to the parameters of the cardiac system in which the invention is implemented. A typical range, as described above, is 2-10 milliseconds. Comparing curves A', B' and C', the frame according to the conventional methods are formed by a single X-ray pulse, whereas the frame according to this invention is formed by a plurality of X-ray pulses.

X-ray radiation often is measured in Roentgens. For the conventional cardiac system, a single frame 40 results from a single pulse 42 of 2-10 millisecond duration at an intensity which results in approximately 20-100 micro-Roentgens as measured at the surface of the image intensifier 30. For the conventional non-cardiac system, a single frame 44 results from a single pulse 46 of approximately 100 millisecond duration at an intensity which results in approximately 1000 micro-Roentgens. For an embodiment according to this invention, a single frame 48 results from a plurality of pulses 50 of 2-10 millisecond duration each at an intensity which for the accumulated pulses results in a total radiation of approximately 1000 micro Roentgens as measured at the surface of the image intensifier 30. Thus, comparing the three types, 20-100 micro-Roentgens, 1000 micro-Roentgens and 1000 micro-Roentgens are generated, respectively.

The generation of a frame 48 having 1000 micro-Roentgens of radiation with a cardiac system according to an embodiment of this invention is achieved by accumulating multiple X-ray exposures to form a single frame. Because the TV camera accumulates all exposure occurring during the accumulation interval, the higher exposure level for such a non-cardiac frame is due to the accumulated effect of multiple exposures occurring over an extended frame time. Accordingly, for an embodiment of this invention, a single frame resulting from approximately 10 pulses of 2-10 milliseconds each may generate a radiation level of approximately 1000 micro-Roentgens. Such exposure level is desireable for achieving high-quality video images.

Modifications to the Conventional Cardiac Angiography System

Figure 4:
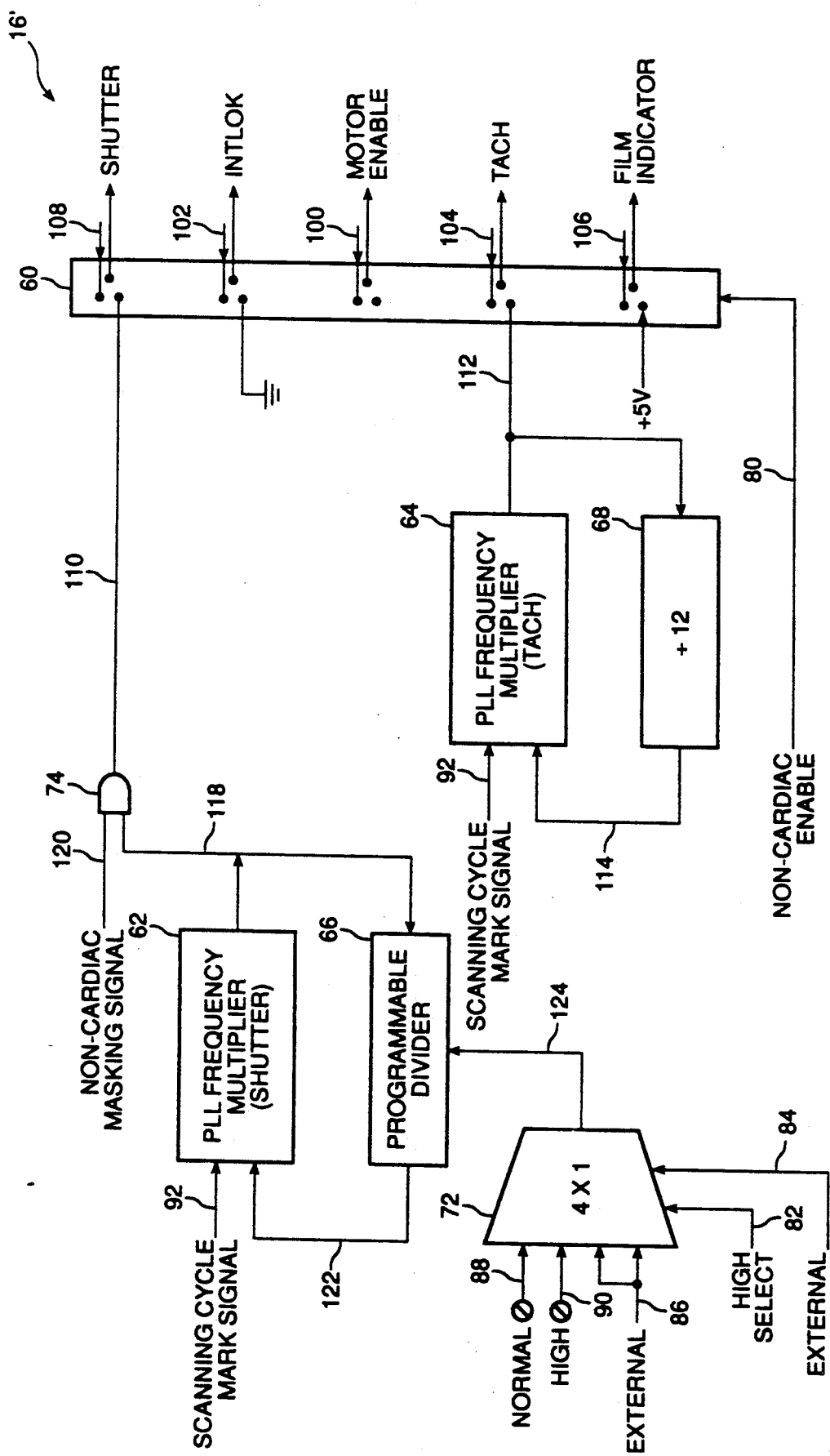
FIG. 4 is a schematic of circuitry added to the system of FIG. 1 for enabling non-cardiac exams to be performed.

FIG. 4 shows a schematic of circuits 16' added to a conventional interface between a computer system 12 and a cardiac imaging system 14. Such conventional interface with the circuits 16' forms the depicted interface 16 (FIG. 1). The added circuits 16' include a switch panel 60, a pair of phase-locked loops 62, 64, a programmable divider 66, a divide-by-12 divider 68, a 4×1 demultiplexor 72, an AND gate 74 and related circuitry (not shown). The functions of the circuits 16' are to select the respective sources of the various film camera control and status signals. These signals include a film camera 34 motor enable signal, a tachometer signal, film camera status signals for film installation (e.g., INTLOK) and film level (e.g., film indicator), and a shutter signal. The shutter signal indicates when an X-ray pulse is to occur. In addition, the circuits 16' function to define a non-cardiac shutter signal which is substituted for the conventional shutter signal to cause a plurality of X-ray pulses during the time an X-ray image is accumulated to form a single image frame.

One input to the circuits 16' is a non-cardiac enable signal 80 which is generated at the operator console 20 in response to an operator input for defining whether the system 10 is to perform a cardiac exam or a non-cardiac exam. During a cardiac exam, the non-cardiac enable signal 80 is inactive. The switch panel 60 responds to the inactive state of the enable signal 80 by positioning the component switches of panel 60 to select the conventional motor control signal 100, the conventional film status and tachometer signals 102, 104, 106, and the conventional film camera shutter signal 108 as the outputs to be routed to the camera controller 36. Each of the signals 100-108 are obtained from the camera controller 36 by modifying the controller 36 to include jumpers in each such signal path. As a result, the corresponding signals returned are the same signals 100-108 as obtained from the controller 36. Thus, for a cardiac exam the shutter signal and the film camera control and status signals are undisturbed.

During a non-cardiac exam, the non-cardiac enable signal 80 is active. The switch panel 60 responds to the active state of the enable signal 80 by positioning the component switches so as to select simulated signals in place of the signals 100-106 and to select the non-cardiac shutter signal 110 in place of the shutter signal 108. The simulated status signals preclude specific built-in alarms of the X-ray imaging system 14 from triggering. Such built-in alarms normally cause the imaging system 14 to shut down or be interrupted. As shown in FIG. 4, the simulated INTLOK is a ground signal, the simulated motor control signal is open circuited so as to disable the motor, and the simulated film indicator is a 5 volt dc signal. The simulated tachometer signal 112 is generated by synchronizing an output signal 114 of a divide-by-12 divider 68 to the TV camera scanning cycle signal 92 at PLL 64. The generation of the remaining signal, the non-cardiac shutter signal 110 is described below.

Generation of the Non-Cardiac Shutter Signal

The non-cardiac shutter signal 110 is formed by the PLL output signal 118 as masked by AND gate 74 and routed to the camera controller 36. The camera controller 36 routes the shutter signal 110 to the X-ray controller 28 for triggering sequential X-ray pulses. For each pulse of the shutter signal, a corresponding X-ray pulse is generated by the X-ray source 26. The non-cardiac shutter signal 110 is shown at curve D of FIG. 5 to be a sequence of pulses 50 which form a frame 48. The shaded portion 116 of each pulse 50 represents a corresponding X-ray pulse generated by X-ray source 26. During the frame 48 the TV camera accumulates the X-ray images corresponding to each of the X-ray pulses emitted.

The formation of the non-cardiac shutter signal 110 now is described further with reference to FIG. 4. PLL 62 receives a scanning cycle mark signal 92 (curve A of FIG. 5) and a programmable divider output signal 122. The scanning cycle mark signal 92 is received from the TV camera 32 and corresponds to the selected scanning speed. For a typical scanning speed, 30 Hz, an active transition in the scanning cycle mark signal occurs every 1/30 seconds. The PLL 62 multiplies the frequency of the scanning cycle mark signal 92 by a programmable factor. For a factor of 3 and a scanning speed of 30 Hz, the multiplication results in a PLL output signal 118 having a frequency of 90 Hz. The PLL output signal 118 is divided by a programmable factor, i.e., 3, at divider 66 to generate a 30 Hz divider output signal 122 which is input to the PLL 62. The PLL 62 synchronizes the divider output signal 22 to the scanning cycle mark signal 92 to generate the PLL output signal 118.

The frequency of the PLL output signal 118 is an X-ray pulse repetition rate, and the PLL output signal 118 is an X-ray pulse repetition rate signal. The PLL output signal 118 is masked at AND gate 74 by a non-cardiac masking signal 120 (see curve C of FIG. 5). The output of the AND gate 74 is the non-cardiac shutter signal 110 (see curve D of FIG. 5).

The non-cardiac masking signal 120 is received from the computer system 12 where it is derived from operator inputs for the image frame width (i.e., 100 ms) and the image rate (e.g., approximately 1 Hz to 8 Hz). The image frame width determines the width of a single masking pulse 121, while the image frame rate determines the frequency of such pulses 121. As the operator may vary the image rate during a non-cardiac exam, the frequency of pulses 121 may vary.

Referring again to FIG. 4, the divider factor for the programmable divider 66 (and thus, multiplication factor for the PLL 62) is determined by the demultiplexor output signal 124. The 4×1 demultiplexor 72 has four channels and two select signals. Each channel defines a divider factor, preferably between 2 and 15. A first channel 88 defines a normal pulse count, a second channel 90 defines a higher pulse count, and the third and fourth channels are tied to a common externally defined pulse count 86. The normal and high pulse counts are defined by respective switches set at installation time. The external pulse count may be defined by the computer system 12 or other source.

One of the defined pulse counts 86, 88, 90 are selected by the high select signal 82 and the external select signal 84 inputs to the demultiplexor 72. The external select signal 84, when active, selects the external pulse count 86 as the demultiplexor output signal 124. When the external select signal 84 is inactive, the high select signal 82 defines whether the demultiplexor output signal 124 is the normal pulse count channel 88 or the high pulse count channel 90.

The computer system 12 defines the respective states of the select signals 82, 84 based upon an operator input for image resolution. According to one embodiment, the TV camera 32 pixel resolution may be selected as either 256×256 pixels, 512×512 pixels or 1024×1024 pixels. If the operator selects either 256×256 pixel resolution or 512×512 pixel resolution, then the normal pulse count is selected. If the operator selects 1024×1024 pixel resolution, then the high pulse count is selected. According to such embodiment, the external pulse count remains a special case—either unused or specially selected.

Non-Cardiac Operation of System 10

To perform a non-cardiac exam, the system operator sets a switch to non-cardiac and inputs data to specify the pixel resolution, the TV camera accumulation interval (i.e., 50 to 100 ms), the image rate (i.e., 1 to 7.5 Hz) and the duration of the acquisition sequence (i.e., 10–15 seconds). Based upon selecting a non-cardiac exam, the non-cardiac enable signal 80 is activated. Based upon the other inputs, the computer system 12 selects and sets an appropriate TV camera scanning speed (i.e., 7.5 Hz, 30 Hz, 60 Hz), generates a non-cardiac masking signal 120, generates the select signals 82, 84 of demultiplexor 72 and generates a TV camera blanking signal.

The activated non-cardiac enable signal 80 triggers the switch panel 60 switches to disable the film camera motor, to select the simulated film camera status signals and to select the non-cardiac shutter signal 110 as the outputs to the camera controller 36. The non-cardiac masking signal 120 is input to the interface 16 at AND gate 74 to mask the PLL output signal 118 so as to generate a non-cardiac shutter signal 110. As previously described, the non-cardiac shutter signal 110 determines the X-ray source triggering. The scanning speed of the TV camera 32 determines the scanning cycle mark signal 92 input from the TV camera 32 to the PLLs 62, 64. The select signals 82, 84 determine the divider factor for programmable divider 66.

Lastly, the blanking signal is generated by the system processor 18 based upon operator inputs which define the accumulation interval and the image rate. The image rate determines the frequency of the blanking signal, while the accumulation interval determines the pulse width. At a lead transition of a blanking signal pulse, the TV camera begins to accumulate X-ray images. At a trailing transition of the blanking signal pulse, the TV camera terminates the accumulation (by scanning the resultant image), forms a video signal for output to the computer system 12, and clears the camera image accumulator for the start of a new image frame. The video image signal is received at the A/D circuit 24 for conversion to digital image data. The resulting digital image data is processed, stored and displayed. At the next lead transition of the blanking signal the TV camera 32 again starts to accumulate X-ray images. Thus, the blanking signal defines the time period for accumulating the X-ray images (e.g., accumulation interval) and triggers the end of an image frame.

According to one application of the embodiment 10, the operator selects a 512×512 pixel resolution, a camera accumulation interval of 100 ms, an image rate of 1 Hz and an acquisition sequence duration of 10 seconds. Based upon these inputs the computer system selects a TV camera scanning rate of 30 Hz and programs the divider 66 to use a normal pulse count set at "3". As a result, the scanning cycle mark signal is a 30 Hz signal and the non-cardiac masking signal is a 1 Hz signal having a pulse width of 100 ms. In addition, the blanking signal is a 1 Hz signal having a pulse width of at least 100 ms. As the computer system 12 generates both the masking signal and the blanking signal, the two signals may be synchronized, and preferably are sychronized or generally synchronized.

The computer system 12 defines the select signals 82, 84 to select the normal pulse count channel 88 based upon the 512×512 pixel resolution. For a normal pulse count defined to cause a divide-by-3 operation, the programmable divider 66 and PLL 62 multiplies the 30

Hz scanning cycle mark signal 92 by three to generate a 90 Hz X-ray pulse repetition rate signal 118. The resulting non-cardiac shutter signal 110 then is a 1 Hz signal carrying a 90 Hz signal during the active portion (e.g., frame 48).

Because the blanking signal and the masking signal 120 are synchronized, the start of the accumulation interval pulse of the blanking signal corresponds to the start of the active portion of the shutter signal 110. Thus, the TV camera 32 accumulates X-ray images of multiple X-ray pulses 116 during the active portion of the shutter signal 110. At the end of the 100 ms pulse of the blanking signal, the accumulated analog video signal at the TV camera 32 is output to the computer system 12 and cleared from the camera to allow exposure for another frame 48. The A/D and image algebra circuitry 24 convert the image signal to digital format, then process and store the digital image data in video memory for concurrent and/or later display on a CRT. Still photographs may be obtained from the digital image data by a printout or hard-copy from the computer system 12.

During a frame 48, the X-ray source 26 generates multiple X-ray pulses 116 according to the pulse sequence specified by the non-cardiac shutter signal 110. The X-ray controller determines the pulse triggering of each X-ray pulse based upon the X-ray pulse repetition rate of the non-cardiac shutter signal 110. The X-ray controller 28 also may determine the X-ray pulse width based upon such shutter signal. The intensity of each pulse is controlled automatically by the feedback loop, including the X-ray source 26, the image intensifier 30 and the X-ray controller 28. According to various embodiments, the X-ray pulse width and/or other X-ray source parameters may be set manually or by the automatic control circuitry.

During a non-cardiac exam, the operator may vary the image rate without altering the accumulation interval or the X-ray pulse repetition rate. According to one application, the sequence begins with one image rate while an injected radio-opaque contrast material (e.g., dye) flows through the venous system. As the dye enters an arterial system of interest, the image rate is increased to a higher rate. Such rate increase causes the time period between accumulation intervals to decrease. As the frequencies of the blanking signal and the masking signal 120 are determined from the image rate, the blanking signal frequency and mask signal frequency increase.

Conclusion

Although a preferred embodiment of the invention has been illustrated and described, various alternatives, modifications and equivalents may be used. For example, although the invention has been described for angiographic applications, the invention may be applied to other radiographic applications also. Therefore, the foregoing description should not be taken as limiting the scope of the inventions which are defined by the appended claims.

What is claimed is:

1. An apparatus for generating a non-cardiac radiograph of a subject with a cardiac angiography system having a TV camera and an X-ray source, the apparatus comprising:
    means for generating a shutter signal from an X-ray pulse repetition rate, an image rate and an image accumulation interval, said X-ray pulse repetition rate being greater than said image rate, said shutter signal determining trigger times for the X-ray source; and
    means for defining a blanking signal for the TV camera, said blanking signal having a frequency determined by said image rate and a pulse width determined by said accumulation interval, wherein a transition of a blanking signal pulse causes the TV camera to terminate an image frame, wherein a plurality of X-ray pulses are generated by the X-ray source prior to the termination of said image frame, and wherein the TV camera accumulates respective X-ray images for each one of said plurality of X-ray pulses prior to said termination of said image frame.

2. The apparatus of claim 1 in which said image rate is a preselected image rate and said accumulation interval is a preselected accumulation interval, and in which the generating means comprises:
    means for generating a non-cardiac masking signal having a frequency determined by said preselected image rate and a pulse width determined by said preselected accumulation interval;
    means for defining an X-ray pulse repetition rate signal having a repetition rate greater than said preselected image rate; and
    means for masking said X-ray pulse repetition rate signal with said non-cardiac masking signal to generate said shutter signal.

3. The apparatus of claim 2, further comprising:
    means for producing a TV camera scanning cycle mark signal having a frequency determined by a TV camera scanning speed; and
    means for synchronizing said X-ray pulse repetition rate signal and said mark signal, and wherein said masking means masks the synchronized X-ray pulse repetition rate signal with said non-cardiac masking signal.

4. The apparatus of claim 3, in which said repetition rate signal defining means comprises a phase-locked loop and a programmable divider, the phase-locked loop multiplying the scanning cycle mark signal by a programmable factor and synchronizing a divider output signal to said mark signal to generate said repetition rate signal, the repetition rate signal input to said divider for being divided by said factor, said factor determined by said scanning speed and a select TV camera pixel resolution.

5. The apparatus of claim 1 in which said cardiac angiography system also has a motorized film camera, the apparatus further comprising means for simulating a film camera status signal and means for disabling the film camera motor while said cardiac angiography system is used to generate a non-cardiac angiograph.

6. A method for generating a non-cardiac radiograph of a subject with a cardiac angiography system having a TV camera and an X-ray source, the method comprising the steps of:
    generating a non-cardiac masking signal having a frequency determined by a preselected image rate and a pulse width determined by a preselected image accumulation interval;
    defining an X-ray pulse repetition rate signal having a repetition rate greater than said preselected image rate; and
    masking said X-ray pulse repetition rate signal with said non-cardiac masking signal to generate a shutter signal, said shutter signal determining trigger times for the X-ray source; and producing a blanking signal for the TV camera, said blanking signal having a frequency determined by said image rate and a pulse width determined by said accumulation interval, wherein a transition of a blanking signal pulse causes the TV camera to terminate an image frame, wherein a plurality of X-ray pulses are generated by the X-ray source prior to the termination of said image frame, and wherein the TV camera accumulates respective X-ray images for each one of said plurality of X-ray pulses prior to said termination of said image frame.

7. The method of claim 6, further comprising the steps of:
producing a TV camera scanning cycle mark signal having a frequency determined by a TV camera scanning speed; and
synchronizing said X-ray pulse repetition rate signal and said mark signal; and
wherein said step of masking is for masking the synchronized X-ray pulse repetition rate signal with said noncardiac masking signal.

8. The method of claim 7, in which the frequency of said repetition rate signal is determined by said mark signal and an image resolution of the TV camera.

9. The method of claim 6 in which said cardiac angiography system also has a motorized film camera, and the method further comprises the steps of:
simulating a film camera status signal and disabling the film camera motor while said cardiac angiography system is used to generate a non-cardiac angiograph.

10. An apparatus for generating a non-cardiac radiograph of a subject with a cardiac angiography system having a TV camera and an X-ray source, the TV camera capturing an image during a camera frame, the apparatus comprising:
means for generating a plurality of X-ray pulses during an accumulation time period;
means for capturing an X-ray image during one camera frame, said X-ray image being an accumulated image caused by said plurality of X-ray pulses.

11. A method for generating a non-cardiac radiograph of a subject with a cardiac angiography system having a TV camera and an X-ray source, the TV camera capturing an image during a camera frame, the method comprising the steps of:
generating a plurality of X-ray pulses during an accumulation time period;
capturing with the TV camera an X-ray image during one camera frame, the X-ray image being an accumulated image caused by said plurality of X-ray pulses.

12. An apparatus for generating a radiograph of a subject, the apparatus comprising:
means for generating a plurality of X-ray pulses during an accumulation time period; and
means for capturing an X-ray image during one frame, said X-ray image being an accumulated image caused by said plurality of X-ray pulses.

13. The apparatus of claim 12 in which said capturing means comprises means for sensing an optical image resulting from one of said plurality of X-ray pulses, said sensing means accumulating each optical image resulting from said plurality of X-ray pulses to accumulate said X-ray image.

14. The apparatus of claim 12, further comprising means coupled to said capturing means and said generating means for synchronizing said capturing means to capture said X-ray image after said accumulation time period.

15. The apparatus of claim 14 in which said synchronizing means comprises:
means for generating a shutter signal from an X-ray pulse repetition rate, an image rate, and an image accumulation interval, said X-ray pulse repetition rate being greater than said image rate, said shutter signal determining trigger times for said X-ray pulse generating means; and
means for defining a blanking signal for the capturing means, said blanking signal having a frequency determined by said image rate and a pulse width determined by said accumulation time period, wherein a transition of a blanking signal pulse causes the capturing means to terminate a frame, wherein a plurality of X-ray pulses are generated by the X-ray pulse generating means prior to the termination of said frame, and wherein the capturing means accumulates an X-ray image in response to said plurality of X-ray pulses prior to said termination of said frame.

16. The apparatus of claim 12 in which said accumulation time period is less than or equal to 100 milliseconds.

17. The apparatus of claim 12 in which each one of said plurality of X-ray pulses has a pulse width of less than or equal to 10 milliseconds.

18. The apparatus of claim 12 in which said frame is less than or equal to one second in duration.

19. The apparatus of claim 16 in which said frame is greater than or equal to two-fifteenths of a second in duration.

20. A method for generating a radiograph of a subject comprising the steps of:
generating a plurality of X-ray pulses during an accumulation time period; and
capturing an X-ray image during one frame, said X-ray image being an accumulated image caused by said plurality of X-ray pulses.

21. The method of claim 20 in which said step of capturing comprises sensing an optical image resulting from one of said plurality of X-ray pulses, a plurality of optical images being accumulated from said plurality of X-ray pulses to generate said X-ray image.

* * * * *